Figures 1, 2:
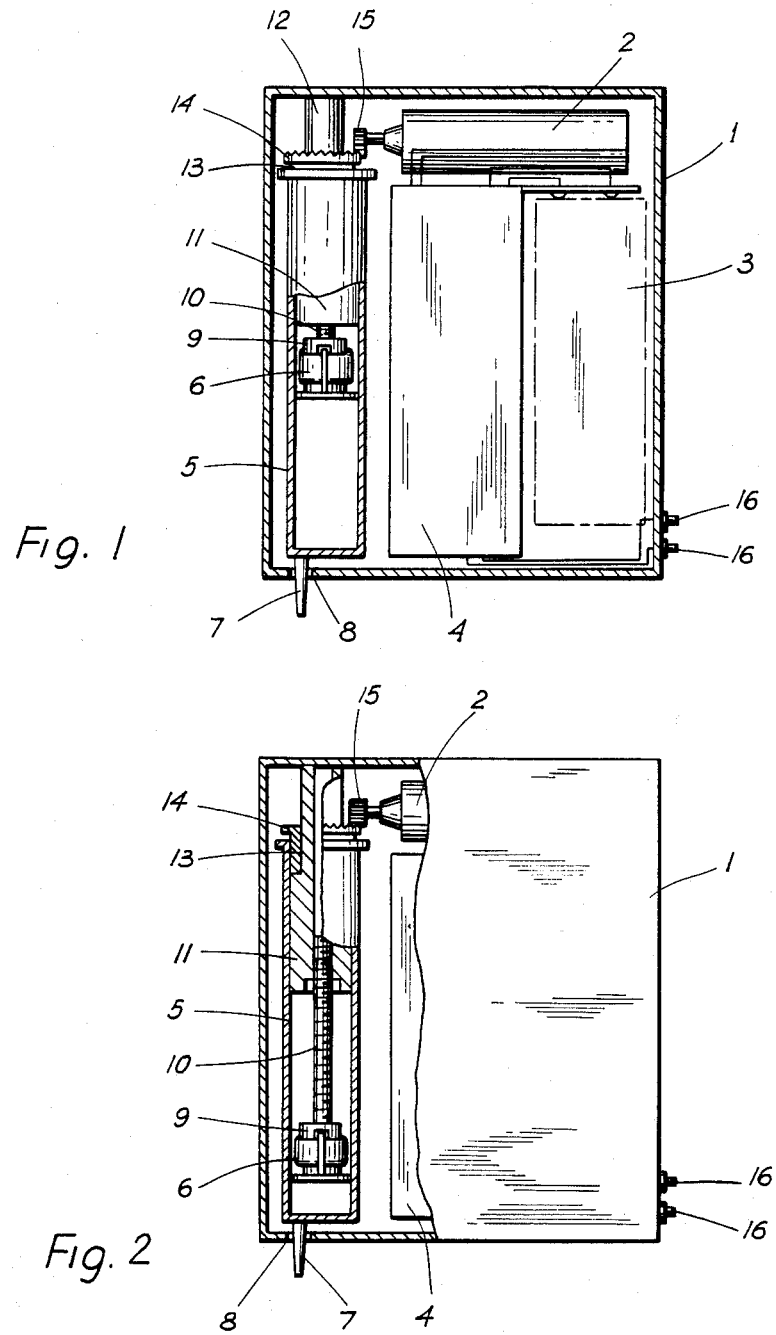

United States Patent [19]

Fernández-Tresguerres Hernandez et al.

[11] Patent Number: 4,619,646
[45] Date of Patent: Oct. 28, 1986

[54] DEVICE FOR THE DELIVERY-DOSING OF INJECTABLE PRODUCTS

[76] Inventors: Jesus A. Fernández-Tresguerres Hernandez; Vincente M. de Garcini Guedas, both of Avda. de los Toreros, 73, 28028 Madrid, Spain

[21] Appl. No.: 693,060

[22] Filed: Jan. 22, 1985

[30] Foreign Application Priority Data

Jan. 25, 1984 [ES] Spain ................................. 277.095

[51] Int. Cl.[4] .............................................. A61M 5/20
[52] U.S. Cl. .................................................... 604/154
[58] Field of Search ..................... 604/155, 154, 151

[56] References Cited

U.S. PATENT DOCUMENTS

| 2,602,446 | 7/1952 | Glass et al. | 604/155 |
| 4,150,672 | 4/1979 | Whitney et al. | 604/155 |
| 4,493,704 | 1/1985 | Beard et al. | 604/154 |

Primary Examiner—John D. Yasko
Attorney, Agent, or Firm—Ladas & Parry

[57] ABSTRACT

The disclosure relates to a device for delivery-dosing of injectable products, the structure has reduced dimensions due mainly to the orthogonal arrangement between the syringe plunger and the output shaft of the electromotor.

3 Claims, 2 Drawing Figures

DEVICE FOR THE DELIVERY-DOSING OF INJECTABLE PRODUCTS

The present invention consists of a device for delivering-dosing an injectable product.

There is currently a large number of patients who must be medicated with injections to be administered in small dosage forms and within very short periods of time.

To carry out this medication and to avoid the continual dependence on professionals and the help of the corresponding centres, there are available delivery-dosage devices which are continuously adapted to the patient's body and which administer the necessary dosage of the drug at pre-programmed periods of time.

These delivery-dosage devices mainly comprise a case incorporating not only an electromotor fed by a dry batter with the help of an electronic programming device or Timer, but also a bag containing the medicament to be dosed which is placed to be expelled outwards through a tube ending in a needle permanently inserted into a vein. With this arrangement and by means of the opportune programme, a determined dosage of the medicament is administered at pre-calculated periods of time.

Besides, there are other devices which administer the medicament since it is contained in a syringe whose movement is produced by an electromotor fed by a dry battery with the help of the corresponding electronic programming device or Timer. However, these devices, since the syringe must be placed in axial alignment with the output shaft of the electromotor, occupy a maximum amount of space and the dimensions of the protective case are large, wherefore they cannot be adapted to the patient's body.

The object of the present invention is to proportion delivery-dosage devices having reduced dimensions, due to the special arrangement of the syringe with respect to the electromotor.

Generally, the present invention consists in placing the syringe in an orthogonal position with respect to the outpute shaft of the electromotor.

Specifically, the plunger of the syringe which is orthogonally disposed with respect to the output shaft of the electromotor, fits into a rod axially threaded to an element fixed in the posterior part of the syringe, which element engages with a friction clutch-type crown wheel with which the pinion disposed in the output shaft of the electromotor meshes. The outlet tube of the syringe in this position passes through the protective case, so that a tube ending in the needle inserted into the patient s vein is connected thereto. The case houses, apart from the syringe and the electromotor, the corresponding dry activating battery and an electronic programming device or Timer with its corresponding actuating controls on the outside, to produce interruption and starting as well as programming thereof.

To complete the description to be made and for a better understanding of the characteristics of the invention, a set of drawings is accompanied to this specification, wherein:

FIG. 1 illustrates a plan view of the delivery-dosage device of the present invention, depicting the case thereof without one of its larger walls.

FIG. 2 corresponds to a plan view, partly cut, depicting the syringe with its plunger in an operative position.

As can be seen from the drawings, the device for dlivering-dosing an injectable product of the present invention comprises a rectangular prismatic case 1 having reduced dimensions, in which the electromotor 2, the dry battery 3 and the electronic programming device or Timer 4 are housed.

The disposable syringe 5 with its corresponding plunger 6 is disposed in an orthogonal position with respect to the electromotor 2. The outlet tube 7 of the syringe 5 cuts across the wall of the case 1 through a bore 8 made therefor.

The plunger 6, preferably consisting of two crossed walls, fits at its free end into two crossed slots of the head 9 of the threaded rod 10 which is axially inserted into an also axial threaded bore of a cylindrical element 11 disposed at the posterior zone of the corresponding tube of the syringe 5.

Element 11 protrudes through the posterior nozzle of the syringe forming a portion 12 having a smaller diameter and determining a stepping on which a friction clutch 13, comprising a bushing provided at its free edge with a crown wheel 14, engages.

The crown wheel 14 constantly meshes with a pinion 15 disposed at the output shaft of the electromotor 2.

The electromotor and the battery 3 are joined by the electronic programming device or Timer 4 provided with two manually operated controls 16 mounted outside the case.

With this structure, operation of the delivery-dosage device of the present invention is as follows:

As illustrated in FIG. 1 of the accompanying drawings, the delivery-dosage device is in its starting position, the Timer 4 having been programmed by manipulating one of the manual controls 16 and having operated same by the other control 16.

Due to the programming of the timer 4, operation of the electromotor 2 will take place at predetermined intervals and for an also determined period of time, depending on the dosage to be administered at each moment.

Once the electromotor 2 is operated, it sends the movement to the crown wheel 14 and this, in turn, to element 11. Since this element 11 is axially blocked against the upper wall of the case, turning thereof will cause the threaded rod 10 to protrude through the lower zone of element 11, whereby the said rod, since it is joined at its head 9 to the posterior zone of the plunger 6, will make the corresponding movement, pushing the product whilst the electromotor 2 operates. When this latter stops functioning by the programming of the timer 4, the product will no longer be administered unless it is operated again due to the auto-operation of the programming device 4.

If for any reason administration cannot take place due to obstruction, the plunger will not necessarily be displaced, since the bushing 13, acting as a friction clutch, will not transmit the rotary movement to element 11 and, consequently, the outlet of the threaded rod 10 will not take place.

This structure proportions a delivery-dosage device having reduced dimensions due mainly to the orthoganal arrangement between the syringe and the electromotor, thereby achieving a device which is easily and simply adapted to the patient's body due precisely to its reduced dimensions.

This type of delivery-dosage device can be employed in any administration of medicaments by injection, although preferably in the corrective treatment of female infertility.

We claim:

1. Device for the delivery-dosing of injectable products comprising a case having reduced dimensions in the interior of which an electromotor with its corresponding feed battery and an electronic programming device or Timer are disposed, the output shaft of the electromotor positioned orthogonally relative to the plunger of a syringe, the outlet tube of which passes through the walls of the case, the plunger at its posterior end fitting into two crossed slots of the head of a rod axially threaded to a cylindrical element located in the posterior zone of the tube of the syringe, which element projects through the nozzle of the syringe forming a portion having a smaller diameter, determining a stepping on which a friction clutch comprised of a bushing provided at its free end with a crown wheel, engages, which wheel constantly meshes with a pinion disposed in the output shaft of the electromotor, the electronic programming device also being provided with two manually operated controls mounted outside the case.

2. A device as in claim 1, wherein the syringe is the sole part which is replaced for each new usage.

3. A device as in claim 1 wherein said syringe is a conventional syringe.

* * * * *